United States Patent
Dongare et al.

(10) Patent No.: US 6,825,388 B2
(45) Date of Patent: Nov. 30, 2004

(54) PROCESS FOR THE PREPARATION OF 4-NITRO-O-XYLENE

(75) Inventors: Mohan Keraba Dongare, Pune (IN); Pratap Tukaram Patil, Pune (IN); Kusum Madhukar Malshe, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/396,102

(22) Filed: Mar. 25, 2003

(65) Prior Publication Data

US 2004/0192977 A1 Sep. 30, 2004

(51) Int. Cl.$^7$ ............................................. C07C 205/00
(52) U.S. Cl. ....................................... 568/940; 568/927
(58) Field of Search .................................. 568/940, 927

(56) References Cited

U.S. PATENT DOCUMENTS 4,415,744 A * 11/1983 Schumacher et al. ......... 560/20
6,376,726 B1 * 4/2002 Choudary et al. .......... 568/927

* cited by examiner

Primary Examiner—J. Parsa
(74) Attorney, Agent, or Firm—Ladas & Parry

(57) ABSTRACT

The present invention relates to the process for vapor phase nitration of o-xylene using dilute nitric acid over H-beta zeolite. More particularly it relates to the selective formation of 4-nitro o-xylene by vapor phase nitration of 0-xylene using dilute nitric acid over commercially available H-beta catalyst. The continuous process of nitration of o-xylene comprises of a reaction carried out in a downflow reactor using o-xylene and dilute nitric acid with mole ratio of 2:1 to 1:2 and WHSV of 0.1–0.5 at 100–250° C. at atmospheric pressure.

13 Claims, No Drawings

PROCESS FOR THE PREPARATION OF 4-NITRO-O-XYLENE

FIELD OF THE INVENTION

The present invention relates to an improved process for the preparation of 4-nitro-o-xylene. More particularly the present invention relates to a process for the selective nitration of o-xylene to 4-nitro-o-xylene, wherein nitration of o-xylene is carried out in vapour phase over zeolite H-beta catalyst using dilute nitric acid as a nitrating agent. The process of present invention gives 4-nitro-o-xylene in with higher yields and selectivity in a continuous process without use of sulfuric acid making it an environment friendly process.

BACKGROUND OF THE INVENTION

Nitration has been an active area of industrial chemistry for over a century. Nitration process is used for production of many large volume nitro aromatics, which are vital intermediates for dyes, pharmaceuticals, perfumes and pesticides.

Nitroxylenes are important because they are readily reduced to corresponding aminoxylenes (xylidines). 4-nitro o-xylene and 3-nitro o-xylenes are industrially important chemical intermediates for the manufacture of corresponding aminoxylenes (Xylidines). 4-amino o-xylene and 3-amino o-xylenes are starting materials for the production of riboflavin and agrochemicals respectively. As compared to 3-nitro-o-xylene, 4-nitro-o-xylene has better commercial and hence is desired by industry.

In the past the catalysts used for the nitration of o-xylene range from zeolites to metal oxides. Reference is made to U.S. Pat. No. 6,376,726 wherein a process for the nitration of o0xylene and other aromatic hydrocarbons is described in liquid phase using fuming nitric acid at reflux temperature and removal of water by Dean-Stark apparatus over modified clay catalysts but the selectivity for 4-nitro-o-xylene was low.

Another process for the nitration of o-xylene in liquid phase (Tomasz et. al. Synth. Commun. 31 (2), (2001) 173–1870) involves the use of 100% nitric acid as nitrating agent over silica supported solid acid catalysts at 20–60° C. but the selectivity for 4-nitro o-xylene was lower. Another process for the nitration of o-xylene (Landau et. al. Catalysts today. 36 (1997) 497–510) is reported by using nitrogen dioxide as nitrating agent at 130° C., WHSV=0.1 h$^{-1}$ over series of zeolites and sulfuric acid supported catalysts and in this case also the selectivity for 4 nitro o-xylene was low.

In the classical method of nitration of o-xylene is performed with nitric acid and environmentally hazardous sulfuric acid gives 3 nitro o-xylene (55%) and 4-nitro o-xylene (45%). One of the major disadvantages of this method is the formation of byproducts of polynitration and also causing environmental pollution during disposal of spent acid.

Most of the reported process have the drawbacks such as, catalyst not being selective for 4 nitro o-xylene, use of fuming nitric acid as a nitrating agent which leads to the oxidation products deactivating the catalyst. Nitrogen dioxide or mixture of sulphuric acid and nitric acid as nitrating agent which makes the process environmentally harmful, removal of water from the reaction mixture making the process tedious, formation of dinitroxylenes which causes problems during separation of the products.

Therefore, it is highly desired to develop a process for the selective preparation of 4-nitro-o-xylene by nitration of o-xylene using nitric acid as well as using solid catalyst to avoid the environmental problem associated with the use of sulphuric acid in the conventional process.

OBJECTS OF THE INVENTION

The main object of the present invention is to provide an improved process for the preparation of 4-nitro-o-xylene by vapor phase nitration of o-xylene using dilute nitric acid over large pore zeolites such as Y-zeolite, Mordenite and Beta zeolite which obviates the drawbacks as mentioned above.

Another object is the use of dilute nitric acid for the reaction, which is easy to handle.

SUMMARY OF THE INVENTION

Accordingly the present invention provides an improved process for the preparation of 4-nitro-o-xylene by reacting a preheated mixture of o-xylene and $HNO_3$ over a solid catalyst followed by condensation to obtain the product, extracting the product with an organic solvent and neutralizing the product using a mild base.

In one embodiment of the present invention, the solid catalyst comprises a large pore zeolites selected from the group consisting of Y-Zeolites, Mordenite and H-beta.

In another embodiment of the invention, the catalyst comprises H-beta zeolite.

In another embodiment of the invention, nitric acid is used in an amount in the range of 10%–50%.

In a further embodiment of the invention, the amount of nitric acid used is about 30%.

In still another embodiment the molar ratio of nitric acid to o-xylene is in the range 2:1 to 1:2 preferably 1:1.5.

In another embodiment the nitration is carried out in an inert gas atmosphere said inert gas being selected from the group consisting of nitrogen, helium and argon.

In yet another embodiment of the invention, the reaction is conducted in a down flow reactor containing inert ceramic packing as preheater and $N_2$ as a carrier gas for a period of 1 to 30 hours at 120 to 180° C.

In yet another embodiment of the invention, condensation is carried out at a temperature in the range of 7–12° C.

In yet another embodiment the reaction is carried out in vapor phase at a temperature in the range of 100 to 250° C., preferably 150° C.

In another embodiment the weight hourly space velocity expressed as grams of organic substrate per gram of catalyst per hour of the reaction mixture varies from 0.1 to 0.5.

In yet another embodiment of the invention, the selectivity for 4-nitro-o-xylene is in the range of 45 to 70%.

DETAILED DESCRIPTION OF THE INVENTION

The present invention provides an improved process for the preparation of 4-nitro-o xylene, which comprises reacting preheated mixture of o-xylene and $HNO_3$ over a catalyst in a conventional down flow reactor containing inert ceramic packing as preheater and $N_2$ as a carrier gas for a period of 1 to 30 hours at 120 to 180° C. and obtaining the product by condensation at 7–12° C., extracting it with a suitable organic solvent and neutralizing it by a mild base. The catalyst is preferably a large pore zeolite such as Y-Zeolites, Mordenite, H-beta, preferably H-beta zeolite. The nitric acid used is preferably in an amount in the range of 10%–50% preferably 30%. In an embodiment the molar ratio of nitric acid to o-xylene is in the range 2:1 to 1:2 preferably 1:1.5 and the vapor phase nitration is carried out at the temperature between 100 to 250° C., preferably 150° C.

The WHSV (weight hourly space velocity expressed as grams of organic substrate per gram of catalyst per hour) of the reaction mixture varies from 0.1 to 0.5. The nitration is carried out in an inert gas atmosphere such as nitrogen, helium or argon, preferably nitrogen.

The process of the present invention is described herein below with reference to the following examples, which are given by the way of illustration and therefore should not be construed as limiting the scope of the present invention in any manner.

EXAMPLE 1

10 g of the catalyst H-beta in the extrudate form was loaded in a tubular glass reactor of 15 mm diameter and 25 cm length. The upper part of the reactor was packed with inert ceramic beads as preheating zone. o-xylene and nitric acid (30%) were fed to the reactor using syringe pumps, Reaction conditions were as follows.
Reaction temperature=150° C.
Carrier gas=$N_2$
Xylene/$HNO_0$=1.5:1 (molar ratio)
WHSV (xylene)=0.17 $h^{-1}$
The products were condensed at 10° C., collected in a receiver extracted with diethyl ether, neutralized by sodium bicarbonate and analyzed by gas chromatography. Results after 25 hours from beginning of reaction are shown below.
Conversion of o-xylene=63.0%
Selectivity for 4-nitro o-xylene=65.4%
Selectivity for 3-nitro o-xylene=21.3%
There was negligible deactivation in catalyst and selectivity during this period.

EXAMPLE 2

10 g of the catalyst H-beta in the extrudate form was loaded in a tubular glass reactor of 15 mm diameter and 25 cm length. The upper part of the reactor was packed with inert ceramic beads as preheating zone. o-xylene and nitric acid (30%) were fed to the reactor using syringe pumps. Reaction conditions were as follows.
Reaction temperature=120° C.
Carrier gas=$N_2$
Xylene/$HNO_3$=1.5:1 (molar ratio)
WHSV (xylene)=0.17 $h^{-1}$
The products were condensed at 10° C., collected in a receiver extracted with diethyl ether, neutralized by sodium bicarbonate and analyzed by gas chromatography. Results after 35 h of the reaction time are given below.
Conversion of o-xylene=49.2%
Selectivity for 4-nitro o-xylene=61.2%
Selectivity for 3-nitro o-xylene=27.5%

EXAMPLE 3

10 g of the catalyst H-beta in the extrudate form was loaded in a tubular glass reactor of 15 mm diameter and 25 cm length. The upper part of the reactor was packed with inert ceramic beads as preheating zone. o-xylene and nitric acid (30%) were fed to the reactor using syringe pumps. Reaction conditions were as follows.
Reaction temperature=180° C.
Carrier gas=$N_0$
Xylene/$HNO_0$=1.5:1 (molar ratio)
WHSV (xylene)=0.17 $h^{-1}$
The products were condensed at 10° C., collected in a receiver extracted with diethyl ether, neutralized by sodium bicarbonate and analyzed by gas chromatography. Results after 25 h of the reaction time are given below.
Conversion of o-xylene=82.3%
Selectivity for 4-nitro o-xylene=49.9%
Selectivity for 3-nitro o-xylene=16.8%

EXAMPLE 4

10 g of the catalyst H-beta in the extrudate from was loaded in a tubular glass reactor of 15 mm diameter and 25 cm length. The upper part of the reactor was packed with inert ceramic beads as preheating zone. o-xylene and nitric acid (30%) were fed to the reactor using syringe pumps. Reaction conditions were as follows.
Reaction temperature=150° C.
Carrier gas=$N_2$
Xylene/$HNO_3$=1.5:1 (molar ratio)
WHSV (xylene)=0.34 $h^{-1}$
The products were condensed at 10° C., collected in a receiver extracted with diethyl ether, neutralized by sodium bicarbonate and analyzed by gas chromatography. Results after 25 h of the reaction time are given below.
Conversion of o-xylene=54.3%
Selectivity for 4-nitro o-xylene=59.6%
Selectivity for 3-nitro o-xylene=28.1%

EXAMPLE 5

10 g of the catalyst H-beta in the extrudate form was loaded in a tubular glass reactor of 15 mm diameter and 25 cm length. The upper part of the reactor was packed with inert ceramic beads as preheating zone. o-xylene and nitric acid (30%) were fed to the reactor using syringe pumps. Reaction conditions were as follows.
Reaction temperature=15° C.
Carrier gas=$N_2$
Xylene/$HNO_3$=0.17 $h^{-1}$
The products were condensed at 10° C., collected in a receiver extracted with diethyl ether, neutralized by sodium bicarbonate and analyzed by gas chromatography. Results after 25 h of the reaction are given below.
Conversion of o-xylene=70.0%
Selectivity for 4-nitro o-xylene=53.4%
Selectivity for 3-nitro o-xylene=20.3%

EXAMPLE 6

10 g of the catalyst H-beta in the extrudate form was loaded in a tubular glass reactor of 15 mm diameter and 25 cm length. The upper part of the reactor was packed with inert ceramic beads as preheating zone. o-xylene and nitric acid (30%) were fed to the reactor using syringe pumps. Reaction conditions were as follows.
Reaction temperature=150° C.
Carrier gas=$N_2$
Xylene/$HNO_3$=2:1 (molar ratio)
WHSV (xylene)=0.17 $h^{-1}$
The products were condensed at 10° C., collected in a receiver extracted with diethyl ether, neutralized by sodium bicarbonate and analyzed by gas chromatography. Results after 25 h of the reaction time are given below.
Conversion of o-xylene=45.8%
Selectivity for 4-nitro o-xylene=60.7%
Selectivity for 3-nitro o-xylene=22.3%

EXAMPLE 7

10 g of the catalyst H-beta in the extrudate form was loaded in a tubular glass reactor of 15 mm diameter and 25 cm length. The upper part of the reactor was packed with inert ceramic beads as preheating zone. o-xylene and nitric acid (50%) were fed to the reactor using syringe pumps. Reaction conditions were as follows.
Reaction temperature=150° C.
Carrier gas=$N_2$
Xylene/$HNO_3$=1.5:1 (molar ratio)
WHSV (xylene)=0.17 $h^{-1}$ The products were condensed at 10° C., collected in a receiver extracted with diethyl ether, neutralized by sodium bicarbonate and analyzed by gas chromatography. Results after 25 h of the reaction time are given below.
Conversion of o-xylene=61.8%
Selectivity for 4-nitro o-xylene=53.2%
Selectivity for 3-nitro o-xylene=20.0%

The main advantages of the present invention are:
1. High selectivity for 4-nitro-o-xylene by nitration of o-xylene using zeolite catalyst.
2. The process produces negligible amount of oxidation products and other by products.
3. The process involves use of dilute nitric acid as a nitrating agent, which is safe and easy to handle.
4. The reaction is carried out at lower temperature.
5. It also gives good conversion of o-xylene along with better selectivity for 4-nitro-o-xylene.
6. No deactivation of the catalyst over length of time.
7. Use of solid acid catalyst, without any use of sulphuric acid as in conventional process making the process environment friendly.

We claim:

1. A process for the preparation of 4-nitro-o-xylene by reacting a preheated mixture of o-xylene and $HNO_3$ over a solid catalyst followed by condensation to obtain the product, extracting the product with an organic solvent and neutralizing the product using a mild base wherein said reaction is carried out in the absence of sulfur compounds and the solid catalyst comprises a large pore zeolite selected from the group consisting of Y-zeolites, Moredenite, and H-beta and mixtures of two or more thereof.

2. A process as claimed in claim 1 wherein the catalyst comprises H-beta zeolite.

3. A process as claimed in claim 1 wherein nitric acid is used in an amount in the range 10%–50%.

4. A process as claimed in claim 3 wherein the amount of nitric acid used is about 30%.

5. A process as claimed in claim 1 wherein the molar ratio of nitric acid to o-xylene is in the range 2:1 to 1:2.

6. A process as claimed in claim 5 wherein the molar ratio of nitric acid to o-xylene is 1:1.5.

7. A process as claimed in claim 1 wherein the nitration is carried out in an inert gas atmosphere, said inert gas being selected from the group consisting of nitrogen, helium and argon and mixtures of two or more thereof.

8. A process as claimed in claim 1 wherein the reaction is conducted in a down flow reactor containing inert ceramic packing as preheater and $N_2$ as a carrier gas for a period of 1 to 30 mhours at 120 to 180° C.

9. A process as claimed in claim 1 wherein the condensation is carried out at a temperature in the range 7–12° C.

10. A process as claimed in claim 1 wherein the process is carried out in vapor phase at a temperature in the range 100 to 250° C.

11. A process as claimed in claim 10 wherein the temperature is about 150° C.

12. A process as claimed in claim 1 wherein the weight hourly space velocity of the reaction mixture varies from 0.1 to 0.5.

13. A process as claimed in claim 1 wherein the selectivity for 4-nitro-o-xylene is in the range 45 to 70%.

* * * * *